United States Patent [19]

Bender et al.

[11] Patent Number: 5,553,484
[45] Date of Patent: Sep. 10, 1996

[54] HIGH FLOW MEMBRANE PROBE

[75] Inventors: William J. H. Bender, Baton Rouge; Gary D. DeLeo, Donaldsonville; Theodore N. Westlake, III, Baton Rouge; Emanuel L. Daigle, Gonzales; Carolyn W. Ribes, Baton Rouge, all of La.

[73] Assignee: The Dow Chemical Company, Midland, Mich.

[21] Appl. No.: 439,909

[22] Filed: May 12, 1995

[51] Int. Cl.⁶ .............................. G01N 1/10; B01D 15/00
[52] U.S. Cl. ................ 73/53.01; 73/864.73; 73/861.04; 73/866.5; 73/61.44; 210/323.2; 210/433.1
[58] Field of Search .............................. 73/53.01, 54.05, 73/61.44, 863.21, 863.41, 863.81, 863.23, 861.04, 864.73, 866.5; 210/323.2, 433.1, 321.72, 321.88

[56] References Cited

U.S. PATENT DOCUMENTS

| | | | |
|---|---|---|---|
| 3,610,418 | 10/1971 | Calderwood | 210/321 |
| 4,356,722 | 11/1982 | Bunce et al. | 73/53 |
| 4,516,580 | 5/1985 | Polanyi | 123/632 |
| 4,629,544 | 12/1986 | Bonaventura et al. | 204/131 |
| 4,715,217 | 12/1987 | Coyne et al. | 73/61.1 |
| 4,779,451 | 10/1988 | Ewaza et al. | 73/53 |
| 4,819,478 | 4/1989 | Melcher | 73/61.1 |
| 4,832,034 | 5/1989 | Pizziconi et al. | 128/632 |
| 4,837,161 | 6/1989 | Stevens et al. | 436/52 |
| 4,957,620 | 9/1990 | Cussler | 210/635 |
| 5,131,266 | 7/1992 | Hassett | 73/61.41 R |
| 5,167,825 | 12/1992 | Lipski et al. | 210/640 |
| 5,317,932 | 6/1994 | Westlake et al. | 73/864.73 |
| 5,442,968 | 8/1995 | Westlake, III et al. | 73/863.23 |

OTHER PUBLICATIONS

Brodbelt et al., *In Vivo Mass Spectrometric Determination of Organic Compounds in Blood with a Membrane Probe*, Analytical Chemistry, vol. 59, No. 3, Feb. 1, 1987, pp. 454–458.

Raimond Peter Cox, *Membrane Inlets for On–Line Liquid–Phase Mass Spectrometric Measurements in Bioreactors*, "Mass Spectrometry in Biotechnological Process Analysis and Control", Plenum Press, 1987 pp. 63–65.

Primary Examiner—Hezron E. Williams
Assistant Examiner—J. David Wiggins

[57] ABSTRACT

A supported capillary membrane separator probe that uses multiple membrane tubes in a parallel configuration connected through common manifolds to the feed and return lines thus allowing greater carrier flow rates to and from the probe resulting in reduced sample lag time from the probe to its analyzer.

2 Claims, 5 Drawing Sheets

HIGH FLOW MEMBRANE PROBE

BACKGROUND OF THE INVENTION

The present invention relates to devices for detecting, monitoring and/or measuring low-level concentrations of certain materials within a complex matrix stream or aggregation of flowable materials. In one of several, more particular aspects, the present invention relates to such devices which employ permeation membrane or diffusion membrane tubing in some fashion to collect and isolate these certain materials from within the stream or aggregation.

Tubular membranes have been suggested for use in this capacity in a number of analytical devices, and are particularly of interest for use in separating out those components of a complex stream or aggregation which might adversely affect a gas or liquid chromatograph or other analytical device if one attempted to analyze the stream or aggregation directly.

Because of the harsh sampling environment presented by many process streams and because of the fragility of the suitable tubular membranes, the previously known devices employing such tubular membranes have very largely been designed to operate on but a portion of the larger stream or aggregation.

Commonly assigned U.S. Pat. No. 5,317,932 describes a device which is amenable to sampling from difficult process streams or aggregations by direct insertion. This feature represents a significant improvement over the previously-known devices. One formerly unresolved problem that the inventors have noted with respect to known direct insertion devices relates to the time taken to obtain a sample of material under review from the source to the analytical device. If the analyzer is in close proximity to the direct insertion device then single conduit direct insertion devices are quite effective. If, on the other hand, the analyzer is located some distance from the direct insertion device then it could take a significant length of time to move an amount of the material under review to the analyzer. This lag time is usually objectionable.

SUMMARY OF THE INVENTION

In considering the above-mentioned problem, the inventors have conceived of an improved apparatus for determining the presence and/or concentration of one or more selected materials in a given stream of flowable materials, such as a matrix stream or other industrial stream. A supported capillary membrane separator probe that uses multiple membrane strands in a parallel configuration connected through common manifolds to the feed and return lines allow greater carrier flow rates to and from the probe resulting in reduced sample lag time from the probe to its analyzer. The high flow membrane probe apparatus comprises a) a support member having a first internal end for inserting into a given stream of flowable material such as a matrix stream and a second end incorporating a manifold cap positioned externally of the matrix stream, the support member underlying and defining a plurality of grooves in and along an external surface thereof, and b) a plurality of conduits designed to be placed in communication with an analytical device external of the given stream of flowable materials such as a matrix stream, and which are positioned and supported individually with one conduit per groove of the plurality of grooves. The selected materials pass through and into the conduits, which are preferably tubular membranes, and are then transported to the analytical device by a supply of a fluid such as an inert carrier gas. "Conduit" as used in describing an element of the present invention above and elsewhere herein, is intended to embrace permeation membrane and diffusion membrane tubing. The tubular membranes of the invention are preferably made from silicone rubber but can also be made from any permeable, semi-permeable, or diffusion material such as polyethylene or Teflon® tubing.

DETAILED DESCRIPTION OF A PREFERRED EMBODIMENT OF THE INVENTION

Figure 1:
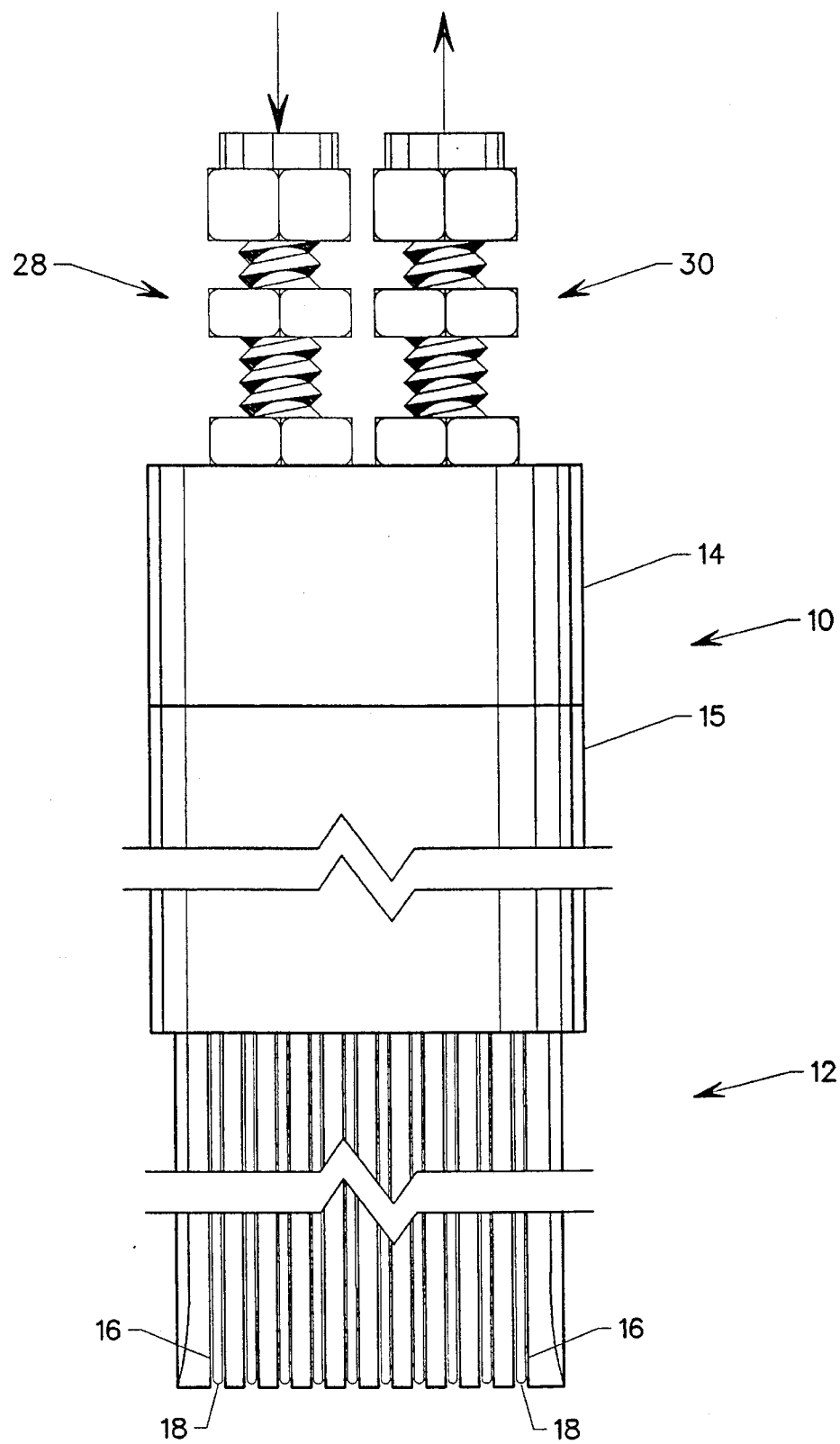
FIG. 1 is a cross sectional top view of the assembled device.

Referring to FIG. 1, the embodiment 10 includes a support member 12, a manifold cap 14, and a header manifold 15. A series of grooves 16 is defined in the support member 12 with a conduit or tubular membrane 18 positioned in each groove 16. A feed line 28 and a return line 30 forming a common header manifold enter the manifold cap 14 providing an entrance for a carrier gas to enter the conduits 18 with the carrier gas and any material that had entered the conduits 18 from the flowable matrix stream being analyzed exiting the conduits 18 through the return line 30 and on to an analytical device not shown.

Figure 2:
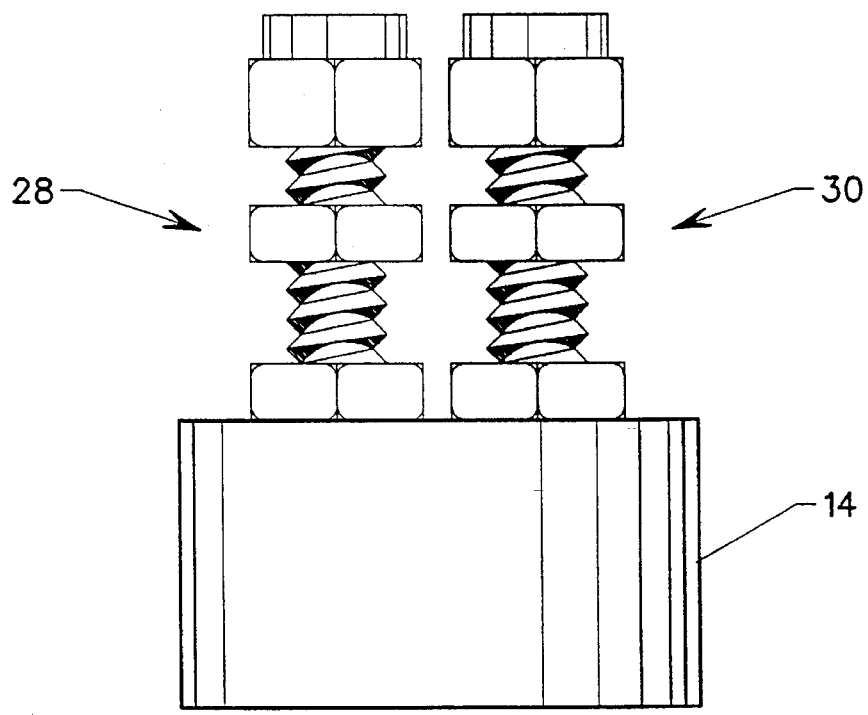
FIG. 2 is a disassembled view of the fluid feed and return manifold cap.
Figure 2A:
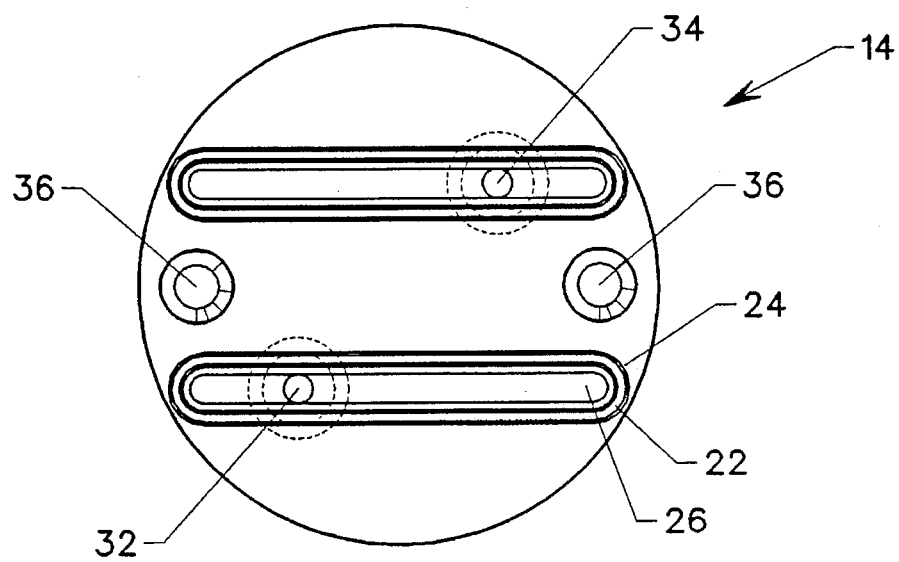

FIG. 2 depicts the manifold cap 14 with the feed line 28 and return line 30. The manifold cap 14 is sealed by a gasket 22, located in a groove 24. Carrier gas from feed line 28 enters the manifold cap 14 through one portal 32 and trough 26 and exits the manifold cap 14 through the other portal 34 to return line 30. The manifold cap 14 is fastened to the manifold 15 through cap mounting holes 36.

Figure 3:
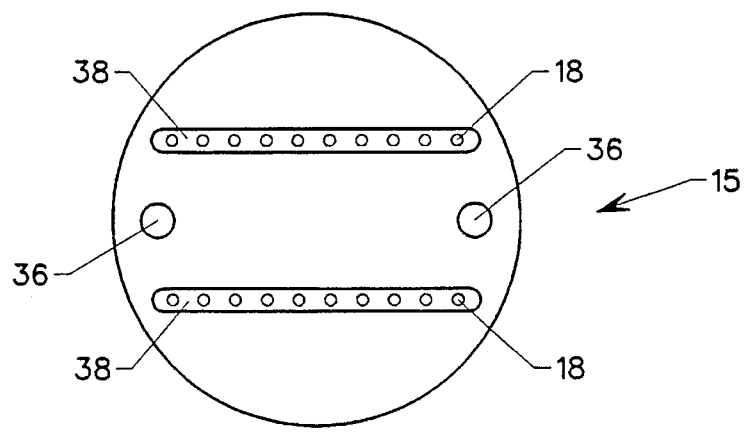
FIG. 3 is a cross sectional top view showing the conduits in the device.
Figure 3A:
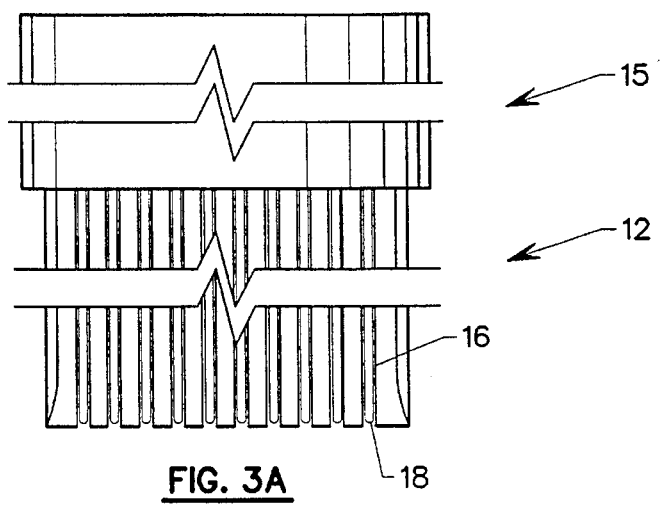
Figure 3B:
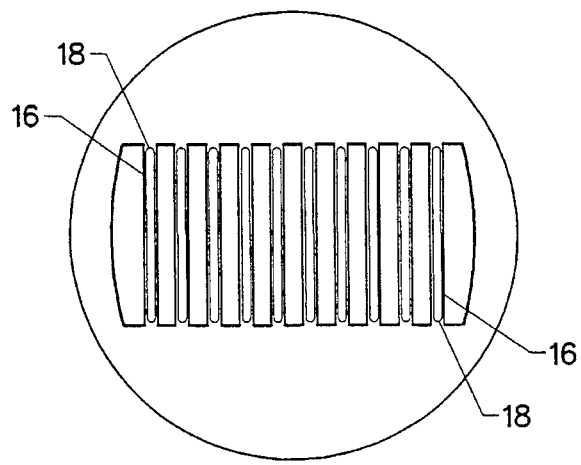

In FIG. 3, individual conduits or tubular membranes 18 are mounted in grooves 16 on the support member 12 and the conduits 18 are cemented in place in the manifold 15 by a cementitious material 38. In this way, the flow of carrier gas to the probe device 10 through feedline 28 is divided into the individual lines in the probe 10, and upon exiting the probe 10, the membranes 18 are recombined to a single return line 30. The manifold 15 is fastened to the manifold cap 14 through cap mounting holes 36.

Figure 4:
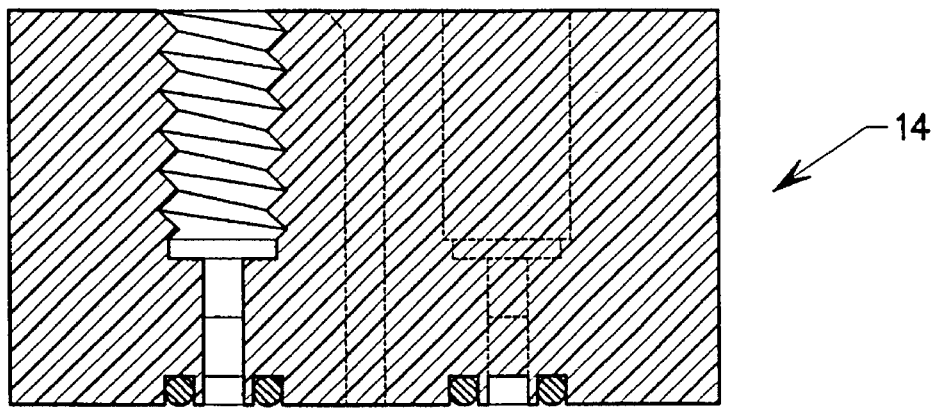
FIG. 4 is a cross sectional side view of the device.
Figure 4A:
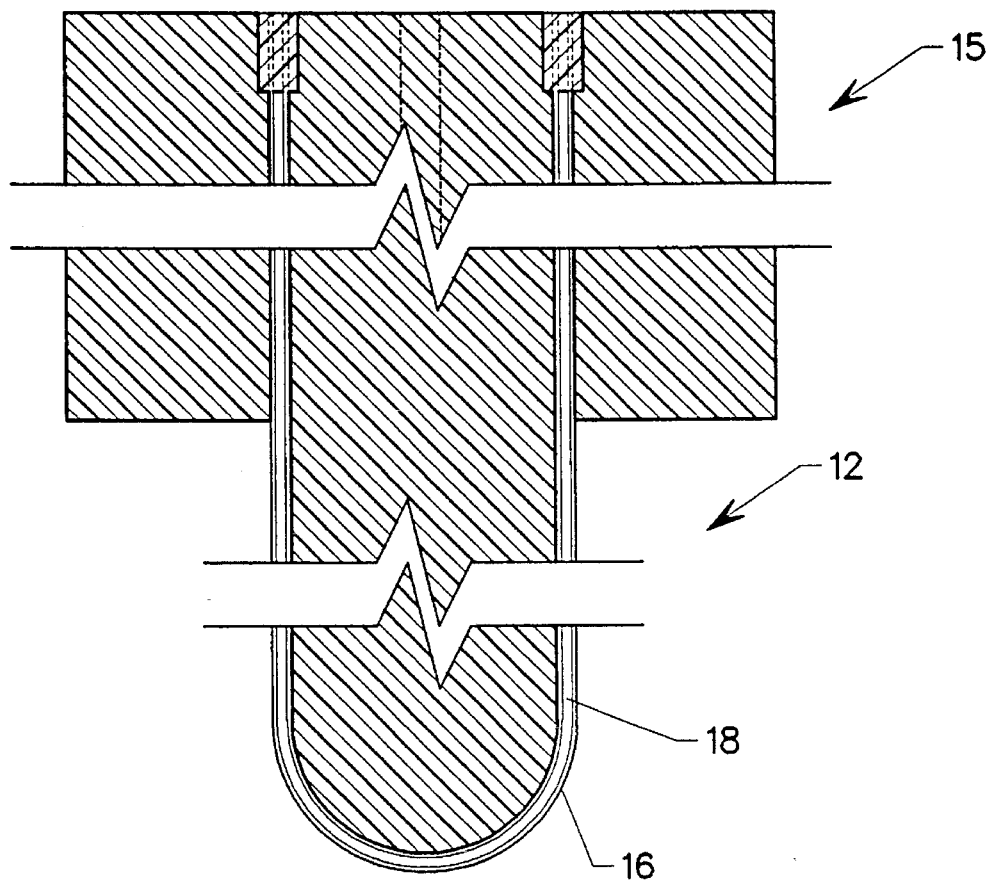

FIG. 4 represents a side view of the probe 10, the support member 12 the manifold cap 14, and the manifold 15. A conduit 18 is shown located within a groove 16 which traverses the entire length of probe 10.

By using multiple strands, the total flow rate of carrier gas in any given conduit 18 is only a fraction of the flow rate in the lines 28, 30 leading to and from the probe 10. If there are, for example, 10 conduits of part 18 then the total flow rate in any given conduit 18 is only 1/10th of the flow rate in the lines to and from the probe 10. By increasing flow rates to and from the probe 10 the lag time associated with carrying a sample from the probe 10 to its associated analyzer can be dramatically reduced thereby allowing the analyzer to be located some distance away from the probe 10 while still responding quickly with the data.

A more complete understanding of the present invention can be gained from the illustrative example used below:

EXAMPLE

A polyether ether ketone (PEEK) body was machined to support ten silicone tubes (0.012" internal diameter) in parallel u-shaped tracks with a common header manifold for gas inlet and outlet. The maximum Argon purge gas flow rate through this particular probe at 25 psig pressure applied to the carrier gas inlet was 3,000 cc/min as compared to eighty cc/min for a probe having a single tube as depicted in U.S. Pat. No. 5,317,932. The silicone tubes were held in place in the manifold with a silicone sealant such as Silicone 734 RTV sealant (Dow Corning, Midland, Mich.). After the sealant had set, the excess tubing and sealant were cut flush with the probe.

A side by side comparison of a probe of the present invention having ten one foot silicone tubes was performed against a standard probe having one ten foot silicone tube. An eight liter covered stainless steel container filled with an aqueous 0.93 ppm chloroform standard at ambient temperature was used for testing the probes. Analysis was performed using an Asea Brown Bovari(ABB) 3100 GC (Gas Chromograph) equipped with a sample loop, an automated ten port gas sampling valve and a flame ionization detector. A Hewlett Packard HP-1 Methyl Silicone Gum Test column (5 meters×0.53 mm Internal Diameter×2.65 Micron film thickness) was operated isothermally at 60 deg. C. The probe was immersed in the aqueous chloroform solution, which was stirred at the maximum setting on a magnetic stirrer. Once the permeation rate had reached equilibrium, the effect of carrier gas flow was studied. Argon carrier gas was circulated through the membrane tubing at 15 psig applied to the carrier gas inlet for the 10×1 foot probe and carried to an automated sample valve. The sample loop was injected onto the chromatographic column, and stream components were separated and quantitated on a flame ionization detector. Injections were made every two minutes and the chromatographic peak integrated by the ABB software. At least six injections were made for each carrier flow rate. To achieve the higher flow rates for the 1×10 foot probe the pressure had to be increased to 25 psig.

Figure 5:
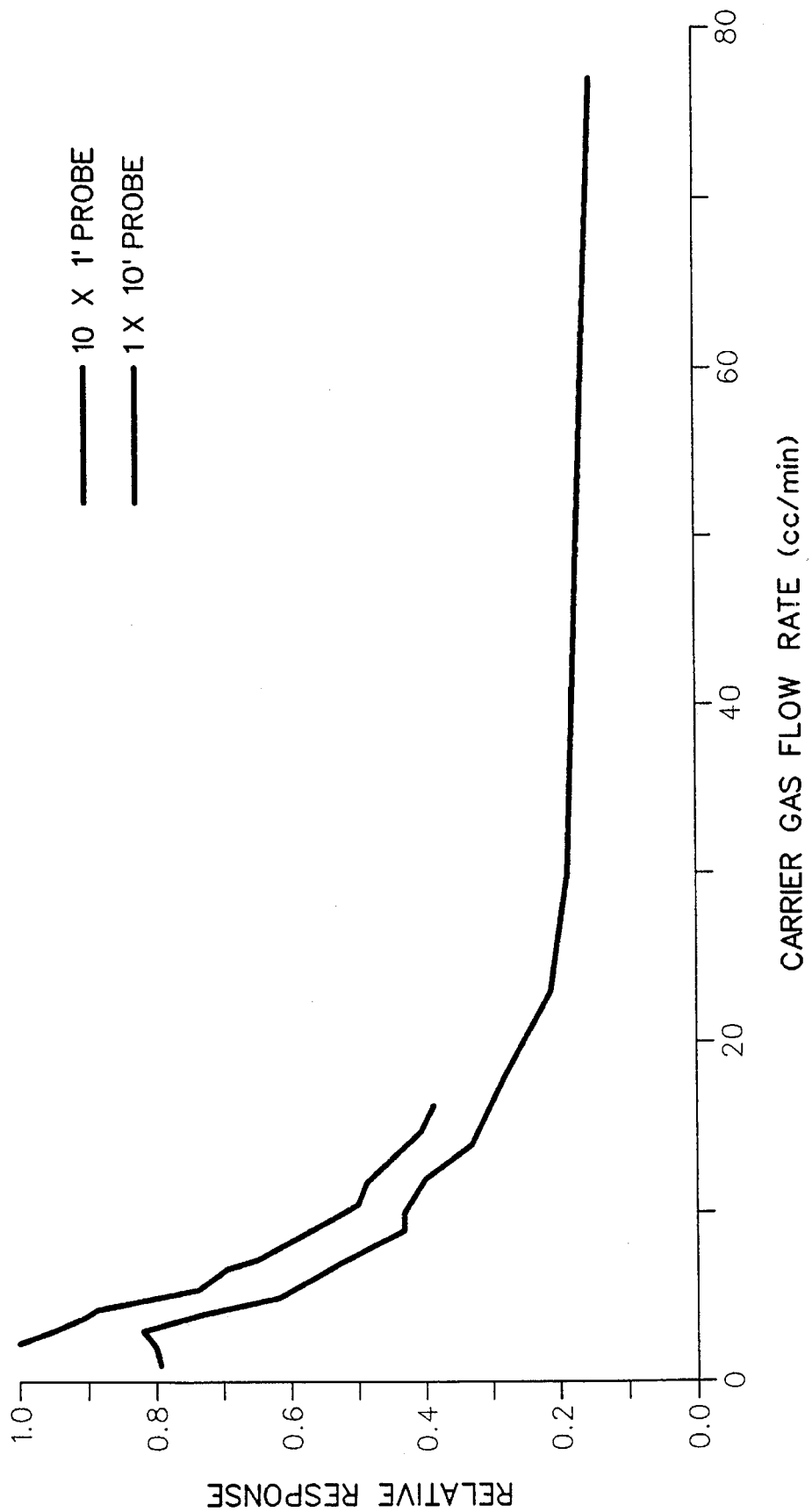
FIG. 5 is a plot of relative response of an analyzer versus carrier gas flow rate.

The flow rate, peak area, and relative response data are shown in Table 1. The relative response was selected by dividing the peak area value by 177, the highest peak area value observed for either probe. The highest flow rate attained with the 1×10' probe was 16.2 cc/min while the 10×1' probe attained 77 cc/min before the testing was terminated. A plot of relative response versus carrier gas flow rate is shown in FIG. 5.

TABLE I

| 10 × 1' PROBE | | | 1 × 10' PROBE | | |
|---|---|---|---|---|---|
| Flow Rate (cc/min) | Peak Area | Relative Response | Flow Rate (cc/min) | Peak Area | Relative Response |
| 1 | 140 | 0.79 | 2.2 | 177 | 1.00 |
| 2 | 141 | 0.80 | 2.9 | 168 | 0.95 |
| 3 | 146 | 0.82 | 3.7 | 161 | 0.91 |
| 4 | 130 | 0.73 | 4.1 | 154 | 0.87 |
| 5 | 110 | 0.62 | 5.4 | 129 | 0.73 |
| 7 | 94 | 0.53 | 6.7 | 123 | 0.69 |
| 9 | 76 | 0.43 | 7.3 | 115 | 0.65 |
| 10 | 76 | 0.43 | 10.5 | 88 | 0.50 |
| 12 | 70 | 0.40 | 11.8 | 85 | 0.48 |
| 14 | 58 | 0.33 | 14.7 | 73 | 0.41 |
| 18 | 49 | 0.28 | 16.2 | 67 | 0.38 |
| 23 | 38 | 0.21 | | | |
| 30 | 34 | 0.19 | | | |
| 77 | 28 | 0.16 | | | |

Using standard ⅛" stainless steel tubing to connect the probe to the analyzer means that the volume inside the tubing is approximately 1 cc per linear foot of tubing. At a flow rate of 16 cc/min it would take 1 minute for the sample to move 16 feet. If the analyzer is 160 feet from the probe then, at 16 cc/min, it would take 10 minutes for the sample to reach the analyzer and this may be unacceptable. In order to decrease this lag time it is necessary to therefore increase the flow rate. By using multiple tubular membranes in the same probe, the flow rate on the system can be significantly increased on the system without damaging the membranes. This allows analyzers to be located at far distances from the probe without any serious lag time problems. For example, at a flow rate of 77 cc/min a sample would reach an analyzer located 77 feet away in one minute. At a flow rate of 500 cc/min, a sample would reach an analyzer located 500 feet away in one minute. This increase in flow rate keeps the lag time in an acceptable range.

While preferred embodiments of the apparatus have been described herein, those skilled in the art will recognize that numerous changes and modifications may be made to these embodiments which are nevertheless within the scope and spirit of the present invention, and which are accordingly intended to be embraced by the claims following hereafter.

What is claimed is:

1. A high flow rate sampling apparatus having a carrier gas inlet, a gas return line outlet and a multitude of fluid flow paths disposed therebetween for use in determining the presence and/or concentration of one or more selected materials in a matrix stream or aggregation of flowable materials comprising:

a) a support member having a first, internal end for inserting into said matrix stream to facilitate fluid flow sampling when said apparatus is placed in service and a second end positioned externally of said matrix stream and wherein said support member underlies and defines a plurality of grooves in and along an external surface thereof of which at least a portion extends into said matrix stream in use;

b) a plurality of conduits which define a multitude of flow paths adapted to be placed in fluid communication with an analytical device external of said matrix stream each of which conduits are positioned and supported individually and substantially wholly within one different groove of said plurality of grooves in said support member extending into said matrix stream whereby said plurality of conduits with associated multitude of flow paths that may be placed in contact with said matrix stream while being protected by and supported within said plurality of grooves; and c) a common header manifold formed from a carrier gas feed line and a return line where said header manifold is mounted in-between the location of said support member and said feed line and said return line for mixing together of said multitude of fluid flow paths.

2. An apparatus as defined in claim 1 having a flow rate of up to about 3,000 cc/min maintained through the plurality of conduits at a pressure of about 25 psig applied to said carrier gas feed line.

* * * * *